(12) United States Patent
Bertone

(10) Patent No.: US 9,649,629 B2
(45) Date of Patent: May 16, 2017

(54) MECHANICALLY SUPPORTING MICROFLUIDIC DEVICES

(75) Inventor: Gary W. Bertone, Southborough, MA (US)

(73) Assignee: Waters Technologies Corporation, Milford, MA (US)

(*) Notice: Subject to any disclaimer, the term of this patent is extended or adjusted under 35 U.S.C. 154(b) by 0 days.

(21) Appl. No.: 14/343,614

(22) PCT Filed: Sep. 7, 2012

(86) PCT No.: PCT/US2012/054240
§ 371 (c)(1),
(2), (4) Date: Jun. 5, 2014

(87) PCT Pub. No.: WO2013/036818
PCT Pub. Date: Mar. 14, 2013

(65) Prior Publication Data
US 2014/0301911 A1 Oct. 9, 2014

Related U.S. Application Data

(60) Provisional application No. 61/531,658, filed on Sep. 7, 2011.

(51) Int. Cl.
| | |
|---|---|
| *G01N 15/06* | (2006.01) |
| *G01N 33/00* | (2006.01) |
| *G01N 33/48* | (2006.01) |
| *B01L 3/00* | (2006.01) |
| *G01N 30/60* | (2006.01) |
| *B01J 19/00* | (2006.01) |

(52) U.S. Cl.
CPC ..... *B01L 3/502707* (2013.01); *B01J 19/0093* (2013.01); *G01N 30/6095* (2013.01); *B01J 2219/00783* (2013.01); *B01J 2219/00804* (2013.01); *B01L 2300/0816* (2013.01)

(58) Field of Classification Search
CPC ......... G01N 15/06; G01N 33/00; G01N 33/48
USPC ....... 422/68.1, 502, 503, 504, 560, 561, 566
See application file for complete search history.

(56) References Cited

U.S. PATENT DOCUMENTS 6,832,787 B1 * 12/2004 Renzi .................. 285/124.1
2003/0223913 A1   12/2003 Karp et al.
(Continued)

FOREIGN PATENT DOCUMENTS

| WO | 2006/043922 A1 | 4/2006 |
|---|---|---|
| WO | 2011/023655 A1 | 3/2011 |

OTHER PUBLICATIONS

International Search Report and Written Opionion mailed on Nov. 23, 2012 for PCT/US2012/54240.
(Continued)

*Primary Examiner* — Brian J Sines
(74) *Attorney, Agent, or Firm* — McCarter & English, LLP; Deborah M. Vernon

(57) ABSTRACT

A microfluidic assembly includes a planar microfluidic separation device and a support body configured to receive the planar microfluidic separation device therein. The support body is configured to apply a substantially distributed compressive preload to a substrate of the planar microfluidic separation device. The compressive preload applied to the planar microfluidic separation device may increase the achievable operating pressure of the planar microfluidic separation device.

16 Claims, 5 Drawing Sheets

(56) References Cited

U.S. PATENT DOCUMENTS

| | | |
|---|---|---|
| 2004/0226884 A1 | 11/2004 | O'Connor et al. |
| 2005/0009101 A1 | 1/2005 | Blackburn |
| 2005/0048669 A1 | 3/2005 | Hobbs et al. |
| 2008/0017306 A1 | 1/2008 | Liu et al. |
| 2008/0055581 A1 | 3/2008 | Rogers et al. |

OTHER PUBLICATIONS

Dong-Jin Shim et al, "Damage and Failure in Silican-Glass-Metal Microfluidic Joints for High-Pressure MEMS Devices," Journal of Microelectromechanical Systems, Feb. 2006, vol. 15, No. 1, p. 246-258.

\* cited by examiner

500

```
┌─────────────────────────────┐
│ Obtain microfluidic assembly│
│ with substantially distributed│
│ compressive preload applied │─ 510
│ to substrate of microfluidic│
│ chemical separation device  │
└──────────────┬──────────────┘
               ▼
┌─────────────────────────────┐
│   Subject device to fluid   │
│  pressure of at least about │
│   2 kpsi during analysis of │─ 520
│  sample without mechanical  │
│      failure of substrate   │
└─────────────────────────────┘
```

FIG. 5

MECHANICALLY SUPPORTING MICROFLUIDIC DEVICES

RELATED APPLICATION

This application is a National Stage Application of International Application No. PCT/US2012/054240, filed Sep. 7, 2012, which claims priority to and benefit of U.S. Provisional Patent Application No. 61/531,658, entitled "Mechanically Supporting Microfluidic Device," filed Sep. 7, 2011, which each of the forgoing applications are incorporated by reference herein in its entirety.

TECHNICAL FIELD

This disclosure relates to mechanically supporting microfluidic devices.

BACKGROUND

Within the field of microscale or nanoscale chromatography, planar microfluidic devices have been gaining interest in recent years as alternatives to stainless steel, polyetherether-ketone (PEEK), or fused silica tubes that are traditionally used for chromatography (e.g., high-performance liquid chromatography (HPLC)) and capillary electrophoresis (CE). CE microchips fabricated in glass or polymers allow for the creation of smaller injection plugs, to better dissipate heat arising from Joule heating, and to integrate multiple parallel separation channels into a single planar device. Likewise, in the HPLC and ultra-high performance liquid chromatography (UHPLC) realm, microchips have several advantages over commercially available tubular columns made out of fused silica or PEEK. Those advantages include the integration of a trapping channel on the same device as the analytical channel with minimum dead volume between the two channels, better ease of use, reduction of fluid connections and associated dead volume, and reduced risk of leakage.

SUMMARY

Some microfluidic devices, such as ceramic and polymeric microfluidic devices, experience mechanical failure (e.g., cracking and/or delamination) of a substrate of the device when subjected to high fluid pressures (e.g., fluid pressures in the range of 10 kpsi to 12 kpsi and greater), thus limiting fluidic channel width, flow rates, and operating pressures for those microfluidic devices. Some embodiments described herein arose, in part, from the inventor's realization that the achievable operating pressures of microfluidic devices can be increased by applying a substantially distributed compressive external stress to a substrate of the device that at least partially counteracts an internal stress applied by elevated fluid pressures within the substrate (e.g., within channels of the substrate). Many brittle materials (e.g., glasses and ceramics) are much stronger in compression than in tension. By applying an external compressive preload to a substrate, an applied elevated fluid pressure within the substrate (e.g., within channels of the substrate) is less likely to result in net tensile stresses in the substrate large enough to cause mechanical failure of the substrate.

In one aspect, a microfluidic assembly includes a planar microfluidic separation device and a support body configured to receive the planar microfluidic separation device therein. The planar microfluidic separation device includes a substrate of a substrate material. The support body includes a material having a greater malleability or a greater elasticity than that of the substrate material. The support body is configured for applying a substantially distributed compressive preload to the substrate of the planar microfluidic separation device that substantially counteracts an internal fluid stress within the substrate of the planar microfluidic separation device under operating conditions, thereby increasing the achievable operating pressure of the planar microfluidic separation device.

In another aspect, a microfluidic assembly includes a planar microfluidic separation device with a substrate and a support body configured to receive the planar microfluidic separation device therein. The support body is configured for applying a substantially distributed multiaxial compressive preload to the substrate of planar microfluidic separation device. The applied substantially distributed compressive preload substantially counteracts an internal fluid stress within the substrate of the planar microfluidic separation device under operating conditions, thereby increasing the achievable operating pressure of the planar microfluidic separation device.

In another aspect, a microfluidic assembly includes a planar microfluidic separation device and a support body configured to receive the planar microfluidic separation device therein. The planar microfluidic separation device includes a substrate of a glass material and/or a ceramic material. The support body is configured for applying a substantially distributed compressive preload of at least about 10 kpsi to the substrate of the planar microfluidic separation device, thereby increasing the achievable operating pressure of the planar microfluidic separation device.

In another aspect, a support body for receiving a planar microfluidic separation device includes a first support member and a second support member. The first support member and the second support member are configured to receive a planar microfluidic separation device therebetween and configured for applying a substantially distributed compressive preload to a substrate of the planar microfluidic separation device, thereby increasing the achievable operating pressure of the planar microfluidic separation device.

In another aspect, chromatography system includes any of the microfluidic assemblies described herein.

In another aspect, a method of performing a chemical separation of a sample includes obtaining a microfluidic assembly. The microfluidic assembly including a planar microfluidic separation device having a substrate subjected to substantially distributed compressive preload. The method further includes subjecting the planar microfluidic separation device to a fluid pressure of at least about 10 kpsi during analysis of a sample without mechanical failure of the substrate.

Embodiments can include one or more of the following features.

In some embodiments, the applied substantially distributed compressive preload is a multiaxial stress. In some embodiments, the applied substantially distributed compressive preload is an applied biaxial stress or an applied triaxial stress.

In some embodiments, the support body includes a first support member and a second support member configured to receive the planar microfluidic separation device therebetween. In some embodiments, the first support member defines a first recess, and the planar microfluidic separation device is disposed at least partially within the first recess. In some embodiments, the second support member defines a second recess, and the planar microfluidic separation device is disposed within a cavity defined by the first and second recesses.

In some embodiments, at least one of the first support member or the second support member defines an aperture for fluid communication with the planar microfluidic separation device. In some embodiments the first support member and the second support member each define a portion of an aperture for fluid communication with the planar microfluidic chemical separating device.

In some embodiments, the support body includes a fitting to provide an interface for connecting fluidic tubing to the planar microfluidic separation device.

In some embodiments, the planar microfluidic separation device comprises a first material having a first coefficient of thermal expansion (CTE). The first support member and/or the second support member includes a second material having a second CTE similar to that of the first CTE. In some embodiments, the second CTE is within $\pm 1.0 \times 10^{-6}$ in/in ° F. of the first CTE. In some embodiments, the second CTE is within $\pm 0.6 \times 10^{-6}$ in/in ° F. of the first CTE.

In some embodiments, the microfluidic assembly includes a semi-compliant material disposed between the support body and the planar microfluidic separation device. The semi-compliant material has at least one of an elasticity greater than that of the support body material or a malleability greater than that of the support body material. In some examples, the semi-compliant material includes a composite of silicone rubber and fiberglass. In some embodiments, the semi-compliant material has a thermal conductivity in a range of about 0.9 W/m-K to 3.5 W/m-K.

In some embodiments, the specified substantially distributed compressive preload is at least about 2 kpsi. In some embodiments, the specified substantially distributed compressive preload is at least about 10 kpsi. In some embodiments, the substantially distributed compressive preload is at least about 12 kpsi. In some embodiments the substantially distributed compressive preload falls within a range of about 2 kpsi to 15 kpsi. In some embodiments the substantially distributed compressive preload falls within a range of about 10 kpsi to 15 kpsi. In some embodiments the substantially distributed compressive preload falls within a range of about 12 kpsi to 15 kpsi.

In some embodiments, the support body is configured for applying sufficient compressive preload to the substrate of the planar microfluidic separation device for operation of the planar microfluidic separation device at a pressure in the range of about 10 kpsi to 12 kpsi. In some embodiments, the support body is configured for applying sufficient compressive preload to the substrate of the planar microfluidic separation device for operation of the planar microfluidic separation device at a pressure in the range of about 12 kpsi to 20 kpsi.

In some embodiments, the substrate of the planar microfluidic device includes one or more of a ceramic material, a glass, a polymer, or a composite.

In some embodiments, the microfluidic assembly further comprises a mechanism for applying a compressive force to at least one of the first support member or the second support member. In some embodiments, at least one of the first support member or the second support member includes a tab configured to receive at least one fastener for exerting a force on at least one of the first support member or the second support member.

In some embodiments, chromatography system is operable to deliver to deliver fluids through the microfluidic assembly at a pressure in the range of about 12 kpsi to 15 kpsi.

In some embodiments, the planar microfluidic separation device is subjected to a fluid pressure of at least about 10 kpsi during analysis of a sample without mechanical failure of the substrate. In some embodiments, the planar microfluidic separation device is subjected to a fluid pressure within the range of about 10 kpsi to 12 kpsi during analysis of the sample without mechanical failure of the substrate. In some embodiments, the planar microfluidic separation device is subjected to a fluid pressure of at least about 12 kpsi during analysis of a sample without mechanical failure of the substrate. In some embodiments, the planar microfluidic separation device is subjected to a fluid pressure within the range of about 12 kpsi to 20 kpsi during analysis of the sample without mechanical failure of the substrate.

Some embodiments can provide one or more of the following advantages.

In some embodiments, the use of a support body to apply a compressive preload to a substrate of a microfluidic device allows the microfluidic device to be operated without mechanical failure of the substrate at pressures higher than if operated without a compressive preload.

In some embodiments, the use of a support body to mechanically support a microfluidic device enables operation with a microfluidic device having a thinner substrate or thinner layers than would be possible without use of the support body.

In some embodiments, cracking and/or delamination of a microfluidic device can be inhibited (e.g., reduced or prevented) by applying a multiaxial compressive preload to a substrate of the microfluidic device using a support body.

Other aspects, features, and advantages of some embodiments are set forth in the description, drawings, and claims.

BRIEF DESCRIPTION OF THE DRAWINGS

FIG. 5 schematically depicts a method of using a microfluidic assembly for chemical separation.

In the drawings like reference numbers indicate like structural elements. The drawings are not necessarily to scale, emphasis instead being placed on illustrating principles of various embodiments.

DETAILED DESCRIPTION

Some embodiments include a support body configured to apply a substantially distributed compressive preload to a substrate of a planar microfluidic separation device, a microfluidic assembly including such a support body, and/or a chromatography system including such a microfluidic assembly. The applied substantially distributed compressive preload may increase the achievable operative pressure of the planar microfluidic separation device as compared to the achievable operative pressure of the planar microfluidic separation device if it were not subjected to a compressive preload.

As used herein the phrase planar microfluidic separation device includes, but is not limited to, chromatographic devices (e.g., high-performance liquid chromatography (HPLC), gas chromatography) and electrophoresis devices (e.g., capillary electrophoresis (CE)). The planar microfluidic separation device may be a planar microfluidic chemical separation device. The planar microfluidic separation device may be used for the separation of ions, molecules, peptides proteins, etc.

Figure 1:
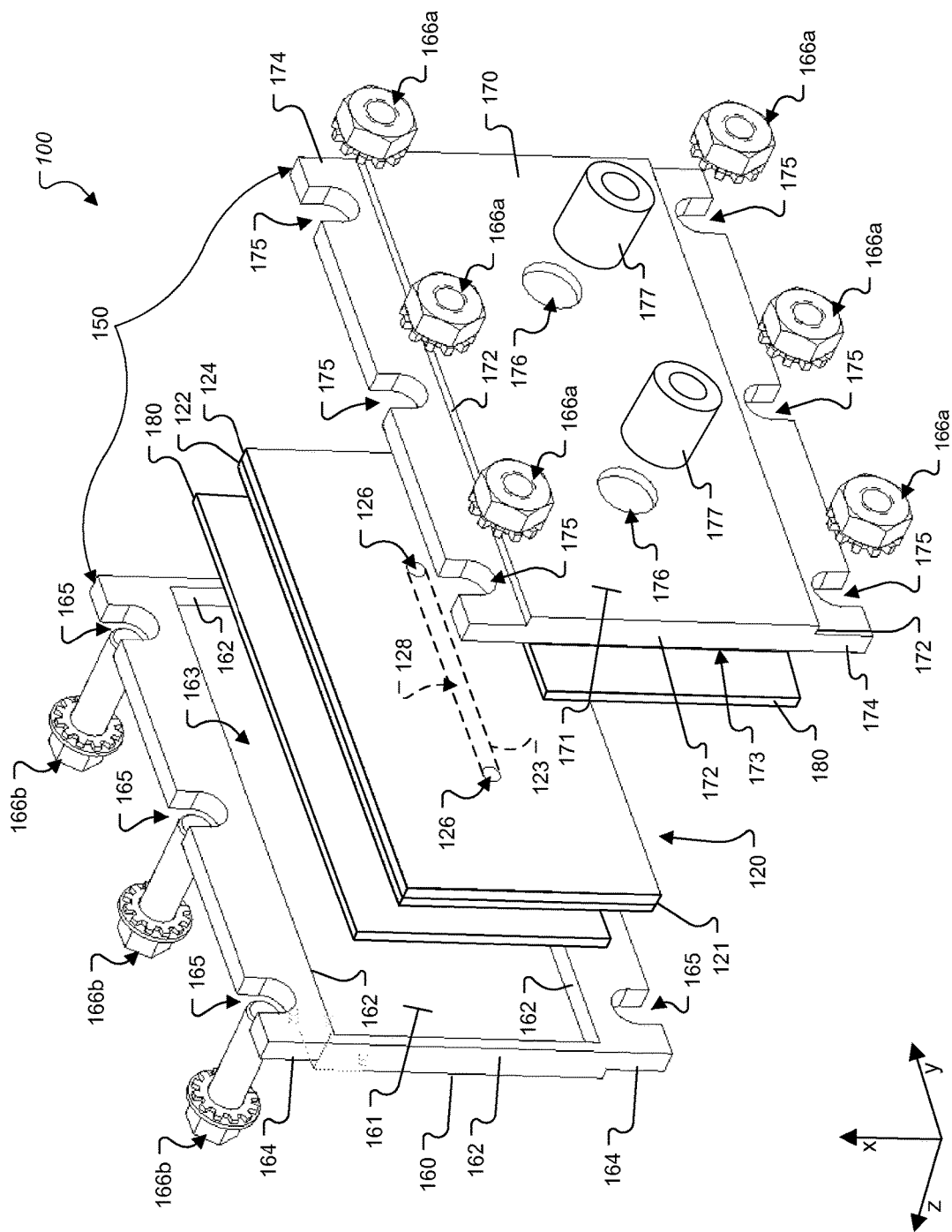
FIG. 1 is an exploded isometric view of a microfluidic assembly, in accordance with some embodiments.

Referring to FIG. 1, in some embodiments, a microfluidic assembly 100 includes a planar microfluidic separation device 120 and a support body 150 for receiving and applying a compressive (e.g. clamping) force on a substrate 121 of the planar microfluidic separation device 120. The substrate 121 of the planar microfluidic separation device can include multiple substrate layers. In the illustrated example, the planar microfluidic separation device 120 includes a first substrate layer 122 and a second substrate layer 124. The first substrate layer 122 can include various materials, such as ceramics (e.g., alumina-based materials, zirconia-based materials, yttria-stabilized zirconia-based materials, low-temperature co-fired ceramics, high temperature co-fired ceramics), glasses, polymers (e.g., polyimide) and/or composites. In some embodiments, the first substrate layer 122 includes a groove 123, which can be formed in the first substrate layer 122 using various methods or techniques, (e.g., by machining, chemical etching, or laser ablation). The second substrate layer 124 can also include various materials, such as ceramics, glasses, polymers and/or composites. The second substrate layer 124 can include the same material(s) or different material(s) than that of the first substrate layer 122. The second substrate layer 124 includes a pair of vias 126 which can be formed in the second substrate layer 124, for example, by machining (e.g., drilling), chemical etching, or laser ablation. In some embodiments, the first substrate layer 122 and the second substrate layer 124 each have a thickness of about 0.0035 inches to about 0.016 inches, and the planar microfluidic separation device 120 has an overall thickness of about 0.070 inches to about 0.101 inches.

As used herein, the term "about" used in conjunction with an identified value (or an identified range) refers to a range encompassing the identified value (or encompassing the identified range) that one of ordinary skill in the art would identify as equivalent to the identified value (or to the identified range).

In some embodiments, the first substrate layer 122 and the second substrate layer 124 are connected together, such as by lamination, to form the substrate 121. When the first substrate layer 122 and the second substrate layer 124 are connected together, the second substrate layer 124 overlies the first substrate layer 122 such that the groove 123 forms an enclosed separation channel 128 and the vias 126 allow for fluid (i.e., liquid and/or gas) communication with the separation channel 128. In some embodiments, the separation channel 128 is packed with chromatographic particles forming at the ends of the separation channel 128 to lock the packed particles in place. In some embodiments, the length of the separation channel ranges between 5 cm and 25 cm, (e.g., about 10 cm). Although the channel is illustrated as being substantially straight, in some embodiments, the separation channel includes one or more turns. The cross-sectional area of the separation channel 128 may be equal to that of commercially available microscale or nanoscale columns, which typically fall in the range of 75 and 300 microns.

In some embodiments, the support body 150 includes a first support member 160 and a second support member 170. The first support member 160 includes a base portion 161 and a plurality of sidewalls 162 that extend upwardly from the base portion to define a first recess 163. In some embodiments, the first support member 160 also includes tabs 164 that extend laterally beyond at least two opposing sidewalls 162. In some embodiments, the tabs 164 define openings 165 for receiving fasteners 166, which may be nut 166a and bolt 166b type fasteners.

In some embodiments, the second support member 170 has a construction similar to that of the first support member 160 including a base portion 171 and a plurality of sidewalls 172 that extend upwardly from the base portion 171 to define a second recess 173. The first and second recesses 163, 173 together are sized to receive the planar microfluidic separation device 120 therebetween. The first support member 160 abuts the second support member 170 such that the first and second recesses 163, 173 define a cavity for enclosing the planar microfluidic separation device 120 therein. The second support member 170 also includes tabs 174 that extend laterally beyond at least two opposing sidewalls 172 of the second support member 170. In some embodiments, the tabs 174 of the second support member 170 define openings 175 that align with the openings 165 in the first support member 160 to accommodate the fasteners 166. During assembly, the fasteners 166 are tightened to fasten the first and second support members 160, 170 together in such a manner as to apply a substantially spatially distributed compressive preload to the planar microfluidic separation device 120.

When a force is applied to the first support member 160 and the second support member 170 using the fasteners (e.g., a uniaxial compressive force along the z-axis) at least some of the surfaces of first support member 160 and the second support member 170 that define the cavity substantially spatially distribute the compressive force over surfaces of the substrate. For example, a surface of the base portion 161 of the first support member distributes the force applied in the negative z-direction over a back surface of the substrate 121 that faces the base portion 161. A surface of the base portion 171 of the second support member distributes the force applied in the z-direction over a front surface of the substrate 121 that faces the base portion 171. If the lateral size (in x and y) of the cavity is only slightly larger than a lateral size of the substrate, lateral expansion (in x and y) of the substrate due to applied compressive stress in the z-direction may be restricted by surfaces of the sidewalls 162 of the first support member and surfaces of the sidewalls 172 of the second support member resulting in a multiaxial (e.g., biaxial or triaxial) compressive stress on the substrate. For example, the reaction force on the lateral surfaces of the substrate preventing lateral expansion can result in stress applied to the lateral faces of the substrate perpendicular to the x-axis or stress applied to the lateral faces of the substrate perpendicular to the y-axis (e.g., biaxial stress), or both. In some embodiments, friction between the surfaces of the base portions of the support members and the top and bottom faces of the substrate may restrict lateral expansion of the substrate contributing to multiaxial stress.

One of ordinary skill in the art recognizes that the designation of the x-direction, the y-direction and the z-direction in the figures and description is arbitrary and chosen merely for illustrative purposes. The identification of the front substrate surface and the back substrate surface is not meant to indicate an orientation in space or an orientation during use, but merely distinguishes substrate surfaces facing the base portions of the first and second support members from substrate surfaces facing the sidewall portions of the first and second support members. Similarly, the identification of lateral substrate surfaces is not meant to indicate an orientation or an orientation during use, but merely identified substrate surfaces facing the sidewall portions of the first and second support members.

In some embodiments, the applied compressive preload is at least about 2 kpsi. In some embodiments the applied compressive preload is at least about 10 kpsi. In some embodiments, the applied compressive preload is at least about 12 kpsi. The applied compressive preload need not be a single preload value. For example, the applied compressive preload may be any preload within a specific range (e.g., within a range of about 2 kpsi to 10 kpsi, about 10 kpsi to about 12 kpsi, about 12 kpsi to about 15 kpsi).

Although microfluidic assembly 100 uses fasteners 166 (e.g., nuts 166a and bolts 166b) for applying a compressive preload to the planer microfluidic chemical separation device 120, in other embodiments, other types of fasteners or fastening mechanisms capable of exerting sufficient force to apply the compressive preload may be employed, (e.g., clamps, clasps, clips, latches, bands). In some embodiments, only one fastener may be employed. Although microfluidic assembly 100 includes separate fasteners 166, in some embodiments, one or more fasteners or fastening mechanisms may be coupled to or integrated into another element of the support body. For example, in some embodiments, one or more fasteners or fastening mechanisms are integral with the first support member, the second support member, or both.

The fasteners or fastening mechanisms may be configured for manual and/or automated application of the compressive preload. For example, in some embodiments, an automated system may be used to adjust a compressive preload in a microfluidic chemical separation device using the fastener or fastening mechanism during assembly before delivery of the device to an end user. In some embodiments, the fastener or fastening mechanism may be used to manually adjust the compressive preload during assembly before delivery of the device to an end user.

In some embodiments, a system of the end user may automatically adjust a compressive preload of the microfluidic chemical separation device using the fastener or fastening mechanism. In some embodiments, the end user may manually adjust a compressive preload of the microfluidic chemical separation device using the fastener or fastening system.

In some embodiments, the second support member 170 defines one or more apertures 176 for fluid communication with the planar microfluidic separation device 120. Coupled about each aperture is a fitting 177. The fittings 177 serve to provide an interface for connecting fluidic tubing to the planar microfluidic separation device 120. In some embodiments, the fittings 177 are configured to self-align microfluidic nozzle tips for fluid communication. For example, in some embodiments, the microfluidic assembly 100 may be arranged and configured for connection with microfluidic nozzles of a fluidic block, such as the type of fluidic block described in International Patent Application No. PCT/US2010/026342, filed 5 Mar. 2010, which published as International Patent Publication No. WO2010/102194 A1 on 10 Sep. 2010, and is incorporated by reference herein in its entirety. Alternatively or additionally, in some embodiments, the fittings 177 include threaded surfaces for mating with a threaded connector, such as a conventional compression screw type fluidic coupling. In some embodiments, the fittings are be made of metal, plastic, ceramic, or any combination of those materials. In some embodiments, the fittings are attached to the second support member (e.g., by welding, by bonding, by mechanical coupling).

The first and second support members 160, 170 can be formed from materials having a greater malleability or a greater elasticity than that of the substrate material. First and second support members can include, but are not limited to, materials such as metals (e.g., stainless steel, titanium, molybdenum, tungsten), high strength plastics (e.g., polyimide (PI), polyamide imide (PAI), polybenzimidazole (PBI), polyetheretherketone (PEEK)), high strength composites (e.g., fiberglass reinforced polymers, carbon-fiber reinforced polymers), and any combination of the aforementioned.

In some embodiments, the first and second support members 160, 170 include a material or materials having a coefficient of thermal expansion (CTE) similar to that of the planar microfluidic separation device 120 (e.g., within $\pm 1.0 \times 10^{-6}$ in/in ° F. or within $\pm 6.0 \times 10^{-6}$ in/in ° F. of that of the substrate of the planar microfluidic separation device), which can help to reduce mechanical stresses over a wide temperature range. For example, in an embodiment in which the planar microfluidic separation device 120 is formed of a ceramic, such as alumina, which has a CTE of about $3.0 \times 10^{-6}$ in/in ° F., the first and second support members 160, 170 can be formed of molybdenum, which has a CTE of about $2.8 \times 10^{-6}$ in/in ° F., or tungsten which has a CTE of about $2.4 \times 10^{-6}$ in/in ° F. For a chemical separation device formed of alumina and first and second support members formed of molybdenum, this would be about a 7% difference in the CTE. For a chemical separation device formed of alumina and first and second support members formed of tungsten, this would be about a 20% difference in the CTE.

In some embodiments, surface irregularities of the planar microfluidic separation device 120 and/or the support body 150 are accommodated by a semi-compliant material 180 disposed between the planar microfluidic separation device 120 and the support body 150. A semi-compliant material has an elasticity greater than that of the support body material, a malleability greater than that of the support body material, or both. In some embodiments, the semi-compliant material 180 is selected for enhanced thermal transfer of heat into or out of the planar microfluidic separation device 120. For example, in some embodiments the semi-compliant material has a thermal conductivity within a range of about 0.9 W/m-K to 3.5 W/m-K. In some embodiments, the semi-compliant material 180 is a sheet-form composite of silicone rubber and fiberglass, such as Sil-Pad® available from The Bergquist Company of Chanhassan Minn. The semi-compliant material could include various materials having suitable material properties, such a polymeric material (e.g., silicone, rubber), a composite material (e.g., a polymer and fiberglass material), a soft metal or metal alloy, or any combination of the aforementioned. Such a sheet-form semi-compliant material can be disposed within the first and/or second recesses.

In embodiments that include a semi-compliant material between the first support body and the planar microfluidic separation device, between the second support body and the planar microfluidic separation device, or both, a difference between the coefficient(s) of thermal expansion (CTE) of the support body material(s) and the CTE of the substrate material may be accommodated, at least in part, by the semi-compliant material. A microfluidic assembly having large differences in coefficients of thermal expansion between support body members and the substrate may employ a semi-compliant material between the support body members and the substrate.

Figure 2:
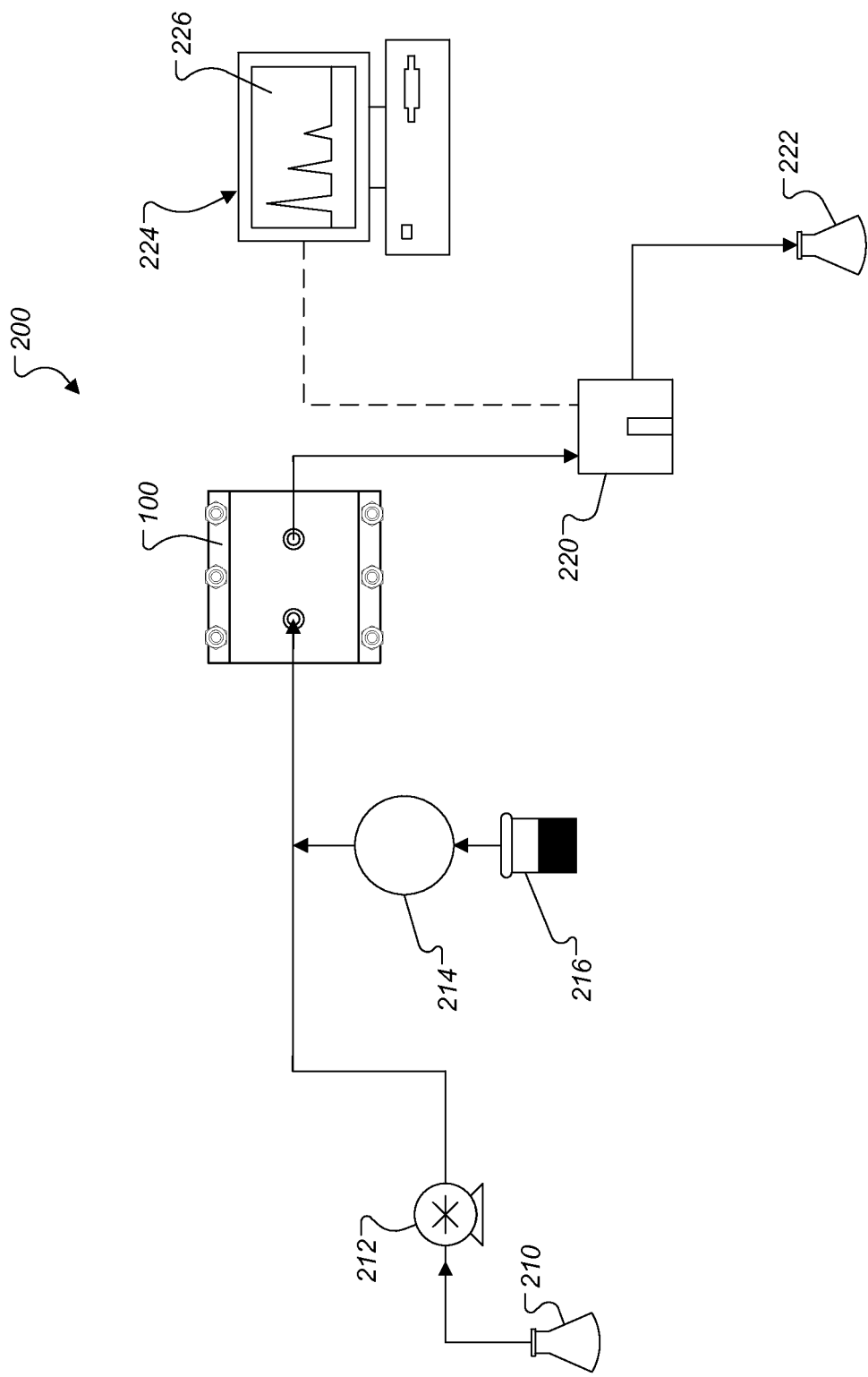
FIG. 2 is a schematic view of a chromatography system including the microfluidic assembly of FIG. 1, in accordance with some embodiments.

A microfluidic assembly 100 with the configuration illustrated in FIG. 1 can be used for performing chemical separation in chromatography systems. For example, FIG. 2 illustrates a liquid chromatography (LC) system 200 that incorporates the microfluidic assembly 100 of FIG. 1. Referring to FIG. 2, a carrier fluid reservoir 210 holds a carrier fluid. A carrier fluid pump 212 is used to generate and meter a specified flow rate of the carrier fluid, typically milliliters per minute. The carrier fluid pump 212 delivers the carrier fluid to an injector 214. The injector 214 accurately and precisely introduces a discrete, predetermined volume of a sample solution, from a sample source 216 (e.g., a sample vial), into the flow of carrier fluid where it can combine with the flow of carrier fluid, which then carries the discrete, predetermined volume of the sample solution into an inlet aperture of the microfluidic assembly 100. The injector 414 can be a simple manual device, a sophisticated autosampler, or have a different configuration. A detector 220 is employed to detect separated compound bands as they elute from the second, outlet aperture of the microfluidic assembly. In some embodiments, the detector 220 includes a UV detector, an evaporative-light-scattering detector (ELSD), a mass spectrometer, and/or a combination thereof. The carrier fluid exits the detector 220 and can be sent to waste 222 or collected, as desired. The detector 220 communicates with a computer data station 224 that records an electrical signal used to generate a chromatogram, which can be displayed on a display 226 of the computer data station 224.

The support body (e.g., support body 150 of FIG. 1) in the microfluidic assembly 100 is configured for application of a substantially distributed compressive preload the planar microfluidic separation device (e.g., device 120 of FIG. 1) such that, during operation, the planar microfluidic separation device is capable of operating at pressures of 10 kpsi and greater (e.g., about 10 kpsi to 12 kpsi, about 12 kpsi to 15 kpsi, about 15 kpsi to 20 kpsi, greater than about 15 kpsi) without mechanically failing (e.g., due to cracking). In some embodiments, the compressive preload is at least about 2 kpsi. In some embodiments, the compressive preload is at least about 10 kpsi. In some embodiments, the compressive preload is in a range of about 2 kpsi to about 10 kpsi. In some embodiment, the compressive preload is in a range of about 10 kpsi to about 12 kpsi. In some embodiments, the compressive preload is in a range of about 12 kpsi to about 15 kpsi.

Figure 3:
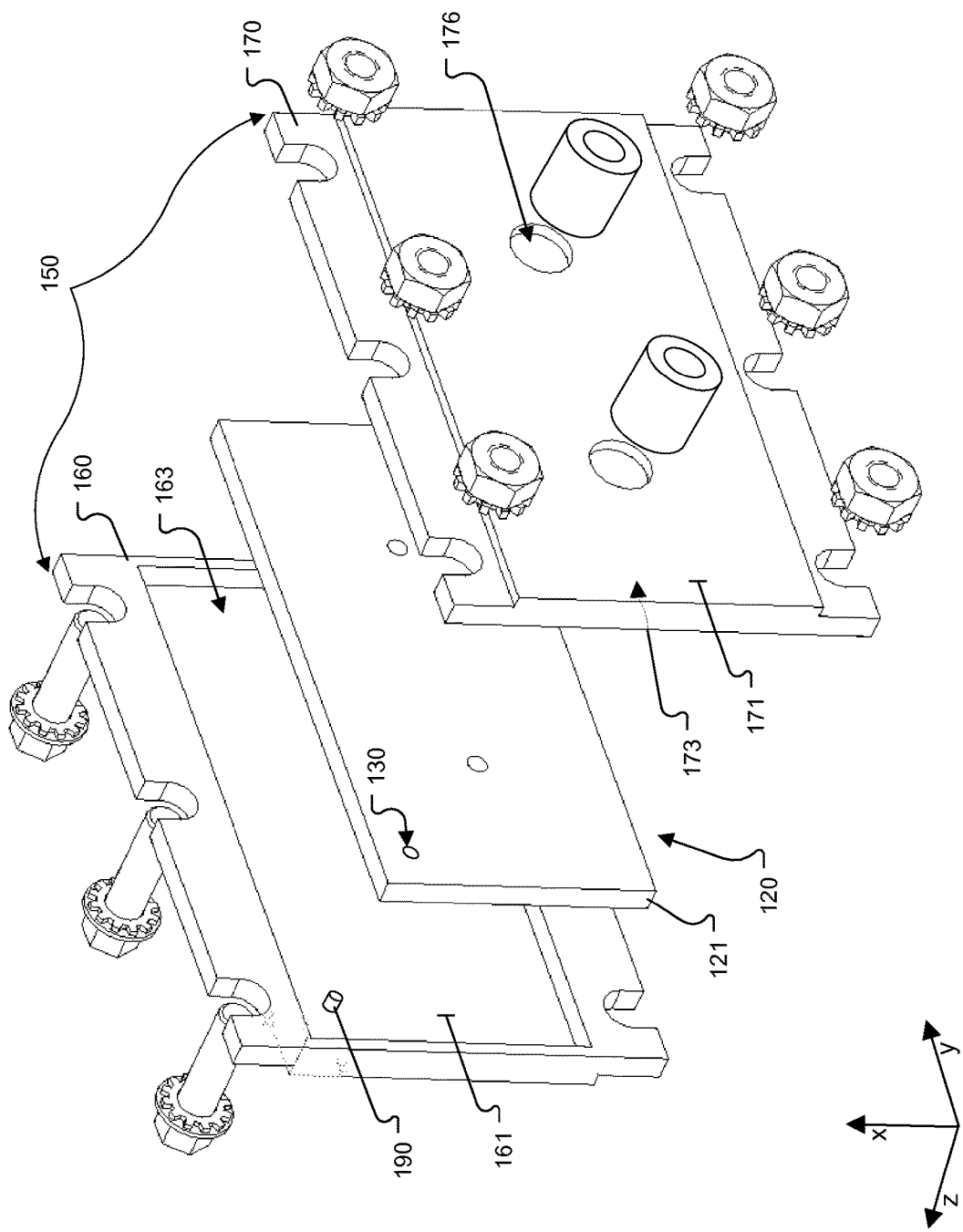
FIG. 3 is an exploded isometric view of a microfluidic assembly that includes alignment features, in accordance with some embodiments.

Some embodiments include additional and/or alternative features as compared to the embodiments described above. For example, as illustrated in the embodiment depicted in FIG. 3, the first and/or second support member 160, 170 can include alignment features, (e.g., alignment pins 190), for aligning the planar microfluidic separation device 120 within the recess 163, 173. In some embodiments, alignment pins 190 (e.g., metal alignment pins) are press fit into corresponding holes in the base portion 161, 171 of the first and/or second support member 160, 170. Such alignment pins 190 can be configured to fit within corresponding holes 130 in the planar microfluidic separation device 120 to aid in proper alignment of the device 120 with the apertures 176 in the support body 150.

Although embodiments described above include fittings for providing an interface for connecting fluidic tubing to a planar microfluidic separation device that are secured to a surface of a support body, in some embodiments, the fittings may alternatively be secured directly to the planar microfluidic separation device and access to the fittings may be provided through the apertures in the support body.

Although embodiments described above are configured for fluid connections to be established off of one surface of a planar microfluidic separation device, some embodiments may be configured for establishing fluid connections off two or more surfaces of a planar microfluidic separation device. For example, a planar microfluidic separation device may have vias on opposing planar surfaces such that fluid enters a first side of the device and exits on a second, opposite side of the device. In this regard, apertures and fittings may be provided in either or both of first and second support members of the support body to allow for fluid communication with the planar microfluidic separation device.

Figure 4:
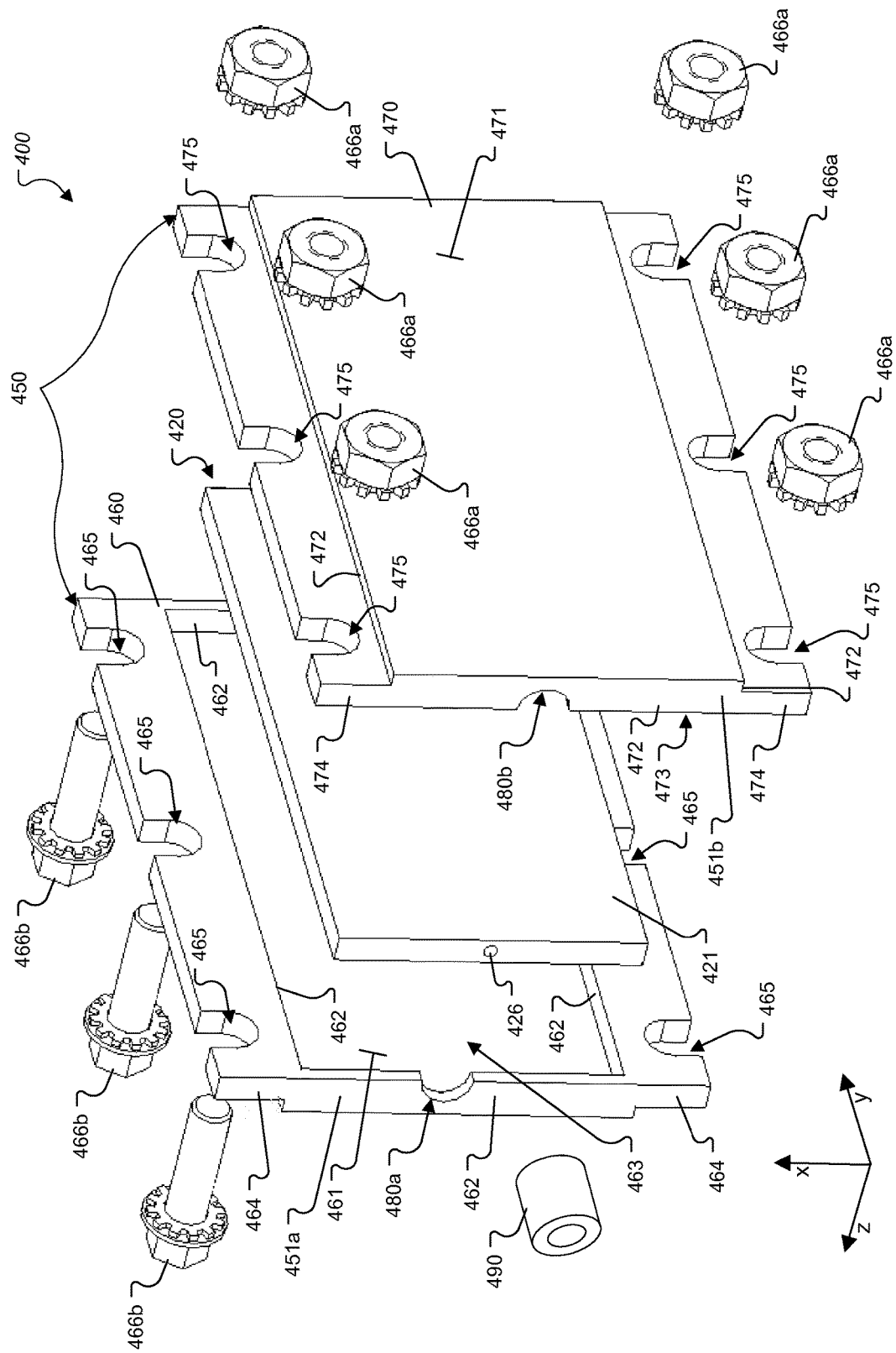
FIG. 4 is an exploded isometric view of a microfluidic assembly that includes end-on fluidics, in accordance with some embodiments.

Although embodiments described above include side-ported fluidics, in some embodiments, a planar microfluidic separation device may alternatively or additionally include one or more fluidic openings on one or more end surfaces. For example, FIG. 4 illustrates an implementation of a microfluidic assembly 400 in which a planar microfluidic separation device 420 includes a fluidic opening 426 through a proximal end surface 427. A second fluid port (not shown) may be provided along the opposite, distal end surface. To accommodate such an arrangement, an aperture 480 is provided along a corresponding end surface 451a, 451b of a support body 450 to allow for fluid communication with the fluidic opening 426 of the planar microfluidic separation device 420. Similar to the embodiment described with regard to FIG. 1, the support body 450 includes first and second support members 460, 470 each including a base portion 461, 471 and sidewalls 462, 472 that define a recess 463, 473 for receiving the device 420, and tabs 464, 474 with openings 465, 475 for accommodating fasteners 466a, 466b (collectively 466) for securing the first and second support members 460, 470 together in such a manner as to preload a substrate 121 of the planar microfluidic separation device 450. To allow for fluid connection to the fluidic opening 426, respective sidewalls 462, 472 of first and second support members 460, 470 of the support body 450 each define a notch 480a, 480b. When the first and second support members 460, 470 are assembled, the notches 480a, 480b together define the aperture 480. In some embodiments, a fitting 490 for providing an interface for connecting fluidic tubing to the planar microfluidic separation device is be secured (e.g., welded or attached with adhesive) to the support body 450 at the aperture 480 after the first and second support members 460, 470 are connected together. Alternatively or additionally, a fitting (not shown) may be secured directly to the planar microfluidic separation device 420 at the fluidic opening 426.

A similar arrangement may be provided at the opposite end of the planar microfluidic separation device 420 to provide fluid communication with end-on fluidic openings. With end-on fluidic openings, the microfluidic assembly 400 can support a straight line column format and provide cartridge-like interchangeability.

Although embodiments described above include first and second support members of a support body that each define an associated recess for accommodating a planar microfluidic separation device therebetween, in some embodiments, only one of the support members defines a recess for accommodating the planar microfluidic separation device. In some embodiments in which only one of the support members defines a recess for accommodating the planar microfluidic separation device, the other support member has a substantially planar construction that overlays and interfaces with the first support member such that a compressive preload is applied to the planar microfluidic separation device.

Although specific reference has been made to the use of microfluidic devices in liquid chromatography systems above, the configurations and concepts described herein also apply to gas chromatography systems, methods and devices.

Although a planar microfluidic separation device consisting of two substrate layers has been described above, the planar microfluidic separation device can consist one layer, or of three or more substrate layers that are laminated together.

Another embodiment includes a method 500 of performing a chemical microfluidic separation of a sample, which is schematically depicted in FIG. 5. Although method 500 may be performed with various types of microfluidic assemblies, support bodies, and systems, for illustrative purposes, method 500 is described herein with respect to assembly 100, planar microfluidic separation device 120, and support body 100 of FIG. 1, and system 200 of FIG. 2. A microfluidic assembly 100 including a microfluidic chemical separation device 120 with a substrate 121 subjected to a substantially distributed compressive preload is obtained (step 510). In some embodiments, the compressive preload is at least a specified preload (e.g., at least about 2 kpsi, at least about 10 kpsi, at least about 12 kpsi). In some embodiments, the compressive preload falls within a range (e.g., a range of about 2 kpsi to 10 kpsi, a range of about 10 kpsi to 12 kpsi, a range of about 12 kpsi to 15 kpsi, a range of about 10 kpsi to 15 kpsi).

In some embodiments, the microfluidic assembly includes a support body 150 and a mechanism (e.g., fasteners 166) that is configured to exert a compressive force on the support body 150, which in turn, exerts a compressive force on the substrate 1221 of the microfluidic chemical separation device.

In some embodiments, the microfluidic assembly 100 is provided with the compressive preload already applied to the substrate 121 of the microfluidic chemical separation device. In other embodiments, obtaining a microfluidic assembly 100 with the compressive preload applied to the substrate 121 comprises obtaining a microfluidic assembly 100 including a support body 150 and a mechanism (e.g., fasteners 166) configured to exert a compressive force on the support body, and using the mechanism to apply a compressive force to the support body, resulting in a compressive preload applied to the substrate of the microfluidic chemical separation device.

The microfluidic chemical separation device is subjected to a fluid pressure of at least about 10 kpsi (e.g., of at least 10 kpsi, of at least about 12 kpsi, of at least about 15 kpsi, of at least about 18 kpsi, within a range of about 10 kpsi to 25 kpsi, within a range of about 10 kpsi to 20 kpsi, within a range of about 12 kpsi to 20 kpsi, within a range of about 15 kpsi to 20 kpsi) during analysis of a sample without mechanical failure of the substrate (step 520). In some embodiments, the fluid pressure of at least about 10 kpsi is sustained throughout analysis of the sample. In some embodiments, the fluid pressure of at least about 10 kpsi is intermittent during analysis of the sample.

Although embodiments of microfluidic assemblies, support bodies, systems, and methods are illustrated and described herein with respect various specific examples, it should be understood by those skilled in the art that various changes and modifications in form and detail may be made without departing from the scope as defined by the following claims.

What is claimed is:

1. A microfluidic assembly comprising:
   a planar microfluidic separation device including a substrate comprising at least one of a glass or a ceramic, the substrate having a working portion including at least one separation channel extending from a channel inlet to a channel outlet; and
   a support body configured to receive the planar microfluidic separation device therein, the support body applies a substantially distributed multiaxial compressive preload of at least about 2 kpsi over the working portion of the substrate of the planar microfluidic separation device to counteract an internal fluid stress within the working portion.

2. The microfluidic assembly of claim 1 wherein the support body comprises a first support member and a second support member, and wherein the first support member and second support member receive the planar microfluidic separation device therebetween.

3. The microfluidic assembly of claim 2, wherein the first support member defines a first recess, and wherein the planar microfluidic separation device is disposed at least partially within the first recess.

4. The microfluidic assembly of claim 3, wherein the second support member defines a second recess, and wherein the planar microfluidic separation device is disposed within a cavity defined by the first recess and the second recess.

5. The microfluidic assembly of claim 2, wherein at least one of the first support member or the second support member at least partially defines an aperture for fluid communication with the planar microfluidic separation device.

6. The microfluidic assembly of claim 1, wherein the support body further comprises a fitting configured to provide an interface for connecting fluidic tubing to the planar microfluidic separation device.

7. The microfluidic assembly of claim 2, wherein the planar microfluidic separation device comprises a first material having a first coefficient of thermal expansion, and wherein at least one of the first support member or the second support member comprises a second material having a second coefficient of thermal expansion within about $\pm 1.0 \times 10^{-6}$ in/in ° F. of the first coefficient of thermal expansion.

8. The microfluidic assembly of claim 7, wherein the second coefficient of thermal expansion is within about $\pm 0.6 \times 10{-6}$ in/in ° F. of the first coefficient of thermal expansion.

9. The microfluidic assembly of claim 1, further comprising a semi-compliant material disposed between the support body and the planar microfluidic separation device, wherein the support body comprises a support body material and wherein the semi-compliant material has at least one of an elasticity greater than that of the support body material or a malleability greater than that of the support body material.

10. The microfluidic assembly of claim 9, wherein the semi-compliant material comprises a composite of silicone rubber and fiberglass.

11. The microfluidic assembly of claim 9, wherein the semi-compliant material has a thermal conductivity within a range of about 0.9 W/m-K to 3.5 W/m-K.

12. The microfluidic assembly of claim 1, wherein the applied substantially distributed multiaxial compressive preload is within a range of about 2 kpsi to 15 kpsi.

13. The microfluidic assembly of claim 1, wherein the support body applies sufficient compressive preload to the substrate of the planar microfluidic separation device for operation of the planar microfluidic separation device at a pressure in the range of about 10 kpsi to 12 kpsi.

14. The microfluidic assembly of claim 1, wherein the applied substantially distributed multiaxial compressive preload is sufficient for operation of the planar microfluidic separation device at a pressure in the range of about 12 kpsi to 20 kpsi without mechanical failure of the assembly.

15. The microfluidic assembly of claim 2, further comprising a mechanism for applying a compressive force to at least one of the first support member or the second support member.

16. The microfluidic assembly of claim 1, wherein the applied substantially distributed multiaxial compressive preload is an applied biaxial stress or an applied triaxial stress.

* * * * *